United States Patent
Suddaby

(10) Patent No.: US 10,322,005 B1
(45) Date of Patent: Jun. 18, 2019

(54) EXPANDABLE INTERVERTEBRAL IMPLANT

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 15/845,111

(22) Filed: Dec. 18, 2017

(51) Int. Cl.
    *A61F 2/44*     (2006.01)
    *A61F 2/46*     (2006.01)
    *A61F 2/30*     (2006.01)

(52) U.S. Cl.
    CPC ............ *A61F 2/4425* (2013.01); *A61F 2/441* (2013.01); *A61F 2/4405* (2013.01); *A61F 2/4611* (2013.01); *A61F 2002/30471* (2013.01); *A61F 2002/30579* (2013.01); *A61F 2002/4625* (2013.01); *A61F 2220/0025* (2013.01)

(58) Field of Classification Search
    CPC .. A61F 2/442; A61F 2/4425; A61F 2002/443; A61F 2/4622; A61F 2002/30535; A61F 2002/30553; A61F 2002/30576; A61F 2002/30579; A61F 2002/30594; A61F 2002/30596; A61F 2002/30598; A61F 2002/30599; A61F 2002/30601; A61F 2/4455; A61F 2/447; A61F 2002/4475
    USPC ............................................. 623/17.11–17.16
    See application file for complete search history.

(56) References Cited

U.S. PATENT DOCUMENTS

| | | | |
|---|---|---|---|
| 5,290,312 A | 3/1994 | Kojimoto et al. | |
| 6,174,334 B1 | 1/2001 | Suddaby | |
| 6,419,705 B1 | 7/2002 | Erickson | |
| 6,562,074 B2 | 5/2003 | Gerbec et al. | |
| 6,648,917 B2 | 11/2003 | Gerbec et al. | |
| 6,830,589 B2 | 12/2004 | Erickson | |
| 6,852,129 B2 | 2/2005 | Gerbec et al. | |
| 6,863,673 B2 | 3/2005 | Gerbec et al. | |
| 7,094,257 B2 | 8/2006 | Mujwid et al. | |
| 7,544,208 B1 | 6/2009 | Mueller et al. | |
| 7,771,473 B2 | 8/2010 | Thramann | |
| 7,811,309 B2 | 10/2010 | Timm et al. | |
| 8,043,376 B2 | 10/2011 | Falahee | |
| 8,241,363 B2 | 8/2012 | Sommerich et al. | |
| 9,283,011 B2 | 3/2016 | Heuer et al. | |
| 9,566,168 B2 * | 2/2017 | Glerum | A61F 2/442 |
| 2015/0320568 A1 | 11/2015 | Ameil et al. | |

* cited by examiner

*Primary Examiner* — Julianna N Harvey
*Assistant Examiner* — Christina Negrellirodriguez
(74) *Attorney, Agent, or Firm* — Simpson & Simpson, PLLC

(57) ABSTRACT

An expandable intervertebral implant, including an inferior component, including a first plate, a second plate connected to the first plate and including a first plurality of locking apertures, and a third plate connected to the first plate and including a second plurality of locking apertures, a superior component slidingly engaged with the inferior component, including a fourth plate, a fifth plate connected to the fourth plate and including a third locking aperture, and a sixth plate connected to the fourth plate and including a fourth locking aperture, and a locking pin assembly arranged at least partially in the third and fourth locking apertures, and operatively arranged to engage the first and second pluralities of locking apertures to lock the expandable intervertebral implant.

22 Claims, 17 Drawing Sheets

EXPANDABLE INTERVERTEBRAL IMPLANT

FIELD

The present disclosure relates to orthopedic surgery, and more particularly to an expandable intervertebral implant serving to improve alignment and spacing between vertebral elements of the spine.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

One common tool used in these spinal surgical procedures is an endoscope. A representative endoscope 30 is shown in FIG. 7A. Endoscopes are complex biomedical devices. The complexity results from the need for fiberoptic bundles and multiple long narrow channels to be contained within a tubular structure that is constrained by the limited dimensions of the body cavity opening. As shown in FIG. 7A, endoscope 30 broadly comprises light guide connector 31, light guide tube 32, control body 33, and insertion tube 34. As will be described infra, the inflatable abrading device of the embodiment is introduced into the disc space via insertion tube 34. As shown in FIG. 7B, surgeon 40 uses the endoscope both to observe and guide the procedure via monitor 41, and to introduce and manipulate surgical instruments and tools during surgery on patient 45.

The endoscope is only one element of the system. Other required elements are a light source, video processor, monitor and water bottle. For the purpose of describing an endoscope in this disclosure, we refer to videoscopes, which represent a newer technology in endoscope development as compared to fiberoptic endoscopes. In videoscopes, the "viewing" fibre bundle is replaced by a miniature charged coupled device (CCD) video camera chip that transmits signals via wires.

Videoscopes include three major sections: connector 31 (sometimes referred to as the "umbilical" section), control body 33 and insertion tube 34. Endoscopes require a watertight internal compartment integrated through all components for electrical wiring and controls, which protects them from exposure to patient secretions during use and facilitates the endoscope being submerged for cleaning and subsequent disinfection. Example embodiments are not intended to be limited to any particular type of endoscope.

Control body 33 provides connections for four systems: the electrical system, the light system, the air and water system, and the suction system. A cable with video signal, light control, and remote switching from the video processor is connected in the electrical system. A watertight cap is required for leak testing and reprocessing. The electrical connector is the only opening to the internal components. The connector is inserted into the light source and directs light via the fiberoptic bundle in the light guide to the distal end of the insertion tube. Air pressure is provided from a pump to the air pipe, and the water bottle is also connected here (there is no water channel or water connection for bronchoscopes). In some endoscope models, the separate air and water channels merge just prior to the distal end where they exit through a single channel. In other models, the air and water channels are totally separate and do not merge. The air and water channels are usually of one millimeter internal diameter, which is too small for brushing. A portable or wall suction system is connected to the suction port. The Universal cord encases the electrical wiring and air, water and suction channels from the connector to the control section. Teflon® (PTFE) tubing is commonly used for channels, and advances in technology have led to more pliable and smooth materials for instrument channels with better anti-adhesion properties. The suction channel size can vary from two to four millimeters internal diameter depending on scope make and model. There is a biopsy port on the side of the insertion tube that allows instruments to be passed down the insertion tube to the distal end (referred to as the instrument channel or biopsy/suction channel).

Control body 33 has moveable knobs that allow the physician to control all scope functions. The angulation control knobs drive the angulation wires and control the bending section at the distal end of the insertion tube, thereby providing two-dimensional angulation. Locking mechanisms are provided to hold the bending section in a specific position. The suction cylinder and valve connects the suction channel to the instrument channel in the insertion tube. By pressing the valve button, suction can be provided to the instrument channel. The air/water cylinder and valve are similar to the suction cylinder/valve except that a two-way button valve is used in a dual channel cylinder thereby providing air or water to the lens at the distal end to wash and insufflate for better vision. Both valves are removable for cleaning. The air and water channels also require a cleaning adapter valve that is to be used at the end of each procedure. Insertion of the cleaning adapter initiates air flow through both air and water channels, and once activated, water is pumped through both channels. The instrument channel port (often referred to as the "biopsy port") is located on the lower part of the control section. It enters the instrument channel at a Y-piece union with the suction channel. A valve is required to close the port so that suctioning may be facilitated. Remote switches present on the top of the control section are usually programmable, allowing control of the video processor (i.e., contrast, iris and image capture functions).

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature. Asymmetric loss of disc space height with degeneration causes adult degenerative scoliosis.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

SUMMARY

According to aspects illustrated herein, there is provided an expandable intervertebral implant, comprising an inferior component, including a first plate, a second plate connected to the first plate and comprising a first plurality of locking apertures, and a third plate connected to the first plate and comprising a second plurality of locking apertures, a superior component slidingly engaged with the inferior component, including a fourth plate, a fifth plate connected to the fourth plate and comprising a third locking aperture, and a sixth plate connected to the fourth plate and comprising a fourth locking aperture, and a locking pin assembly arranged at least partially in the third and fourth locking apertures, and operatively arranged to engage the first and second pluralities of locking apertures to lock the expandable intervertebral implant.

According to aspects illustrated herein, there is provided an expandable intervertebral implant, comprising an inferior component, including a first plate, a second plate connected to the first plate and comprising a first plurality of locking apertures, and a third plate connected to the first plate and comprising a second plurality of locking apertures, a superior component slidingly engaged with the inferior component, including a fourth plate, a fifth plate connected to the fourth plate and comprising a third locking aperture, the fourth plate arranged adjacent the second plate, and a sixth plate connected to the fourth plate and comprising a fourth locking aperture, the sixth plate arranged adjacent the third plate, and a locking pin assembly, including a shaft having a first end and a second end, a first engaging member sliding engaged with the first end and arranged at least partially in the third locking aperture, a second engaging member sliding engaged with the second end and arranged at least partially in the fourth locking aperture, and at least one spring arranged axially between the first and second engaging members, wherein the first and second engaging members are operatively arranged to engage the first and second pluralities of locking apertures to lock the expandable intervertebral implant.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1:
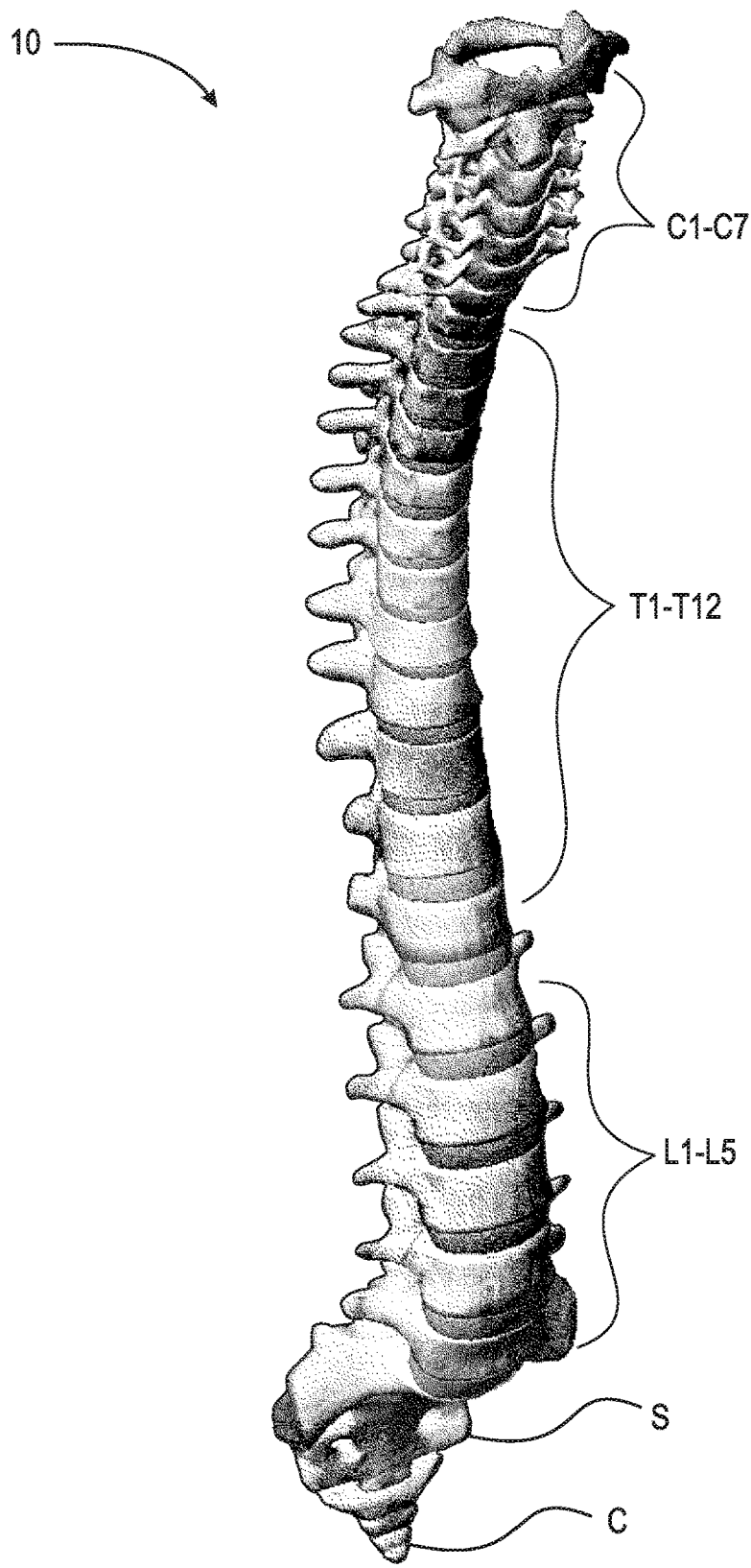
FIG. 1 is an anterior perspective view of a spinal column.
Figure 2:
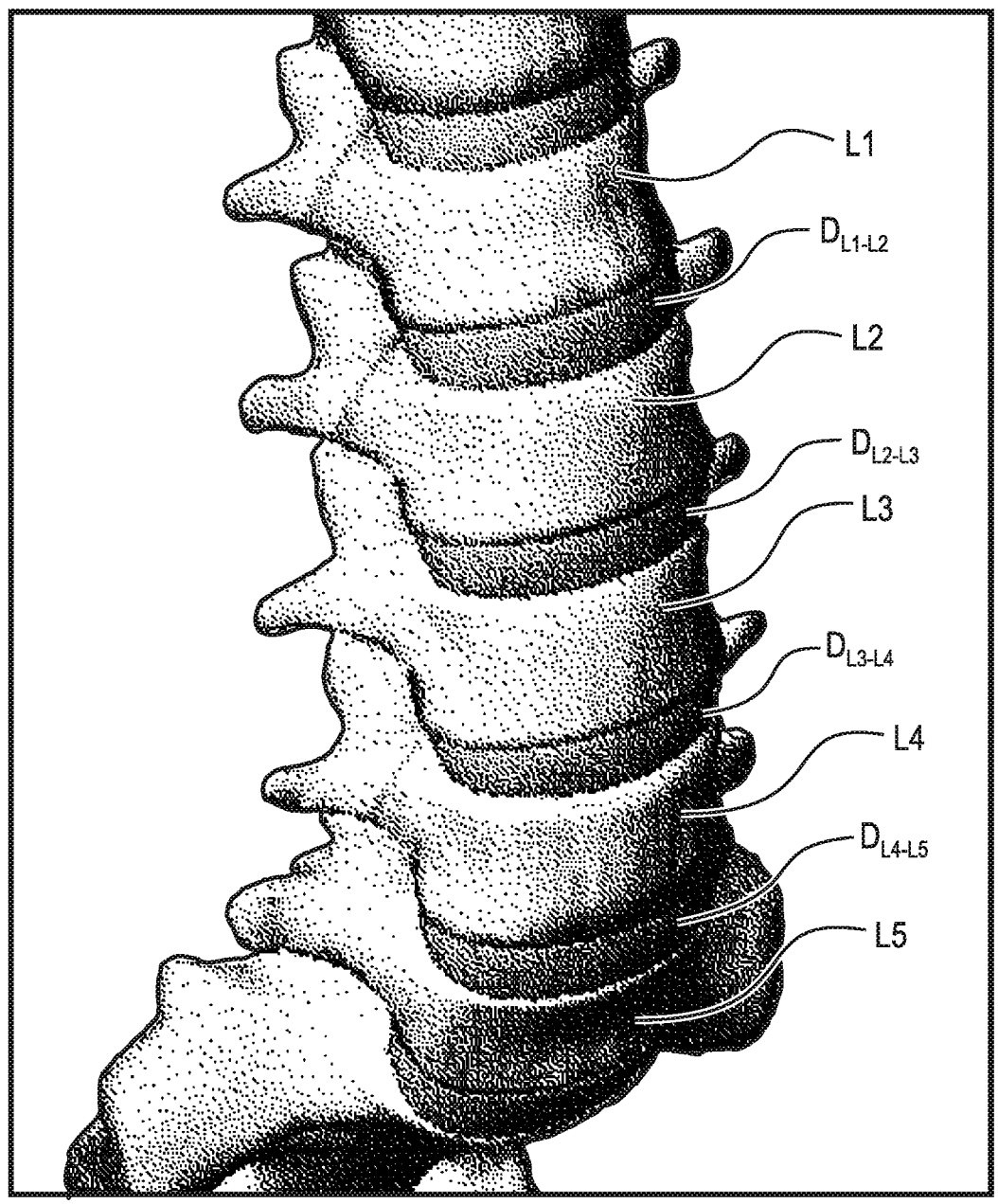
FIG. 2 is an anterior perspective view of the lumbar section of the spinal column shown in FIG. 1.
Figure 3:
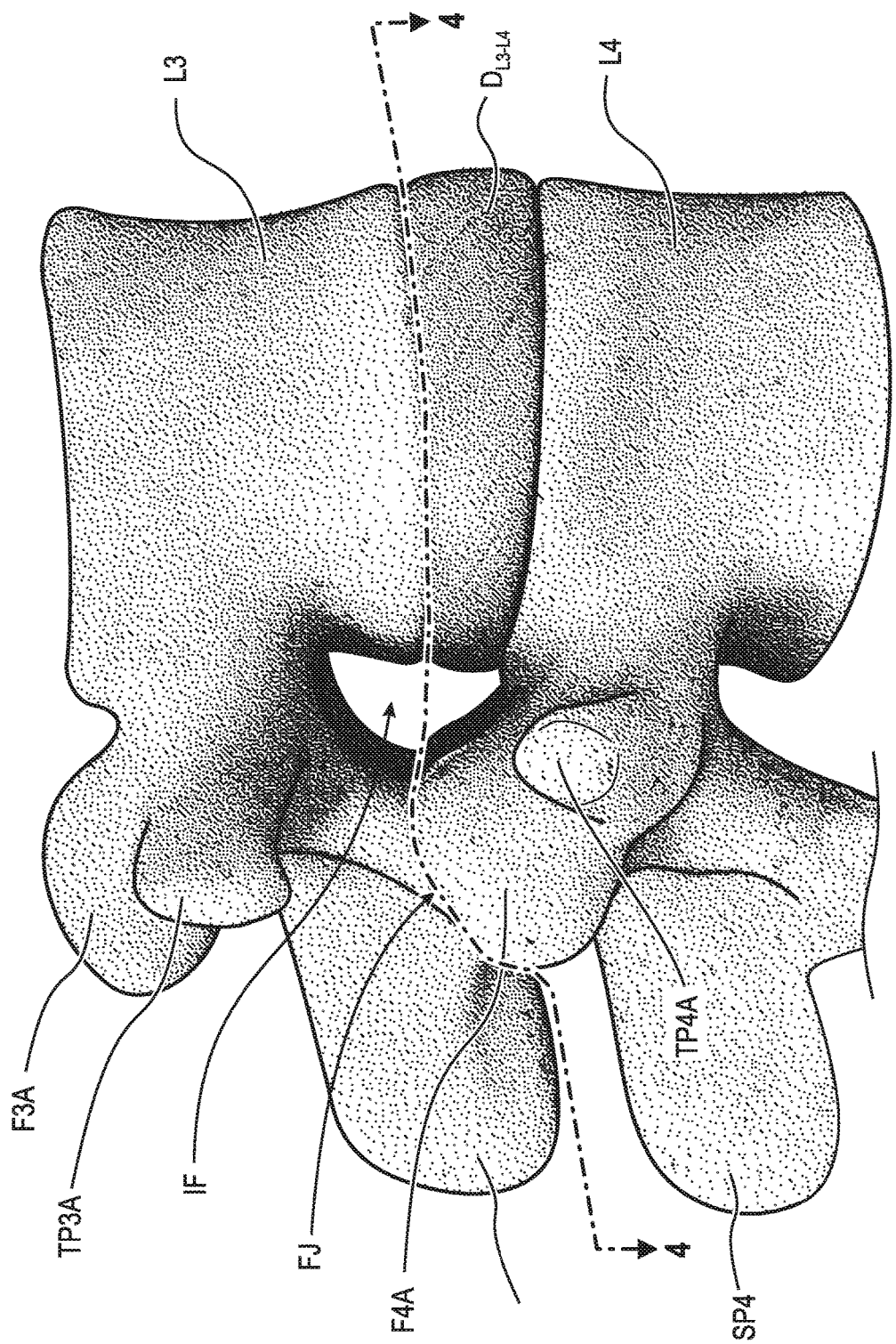
FIG. 3 is a lateral perspective view of two vertebrae, a disc, and related spinal anatomy.
Figure 4:
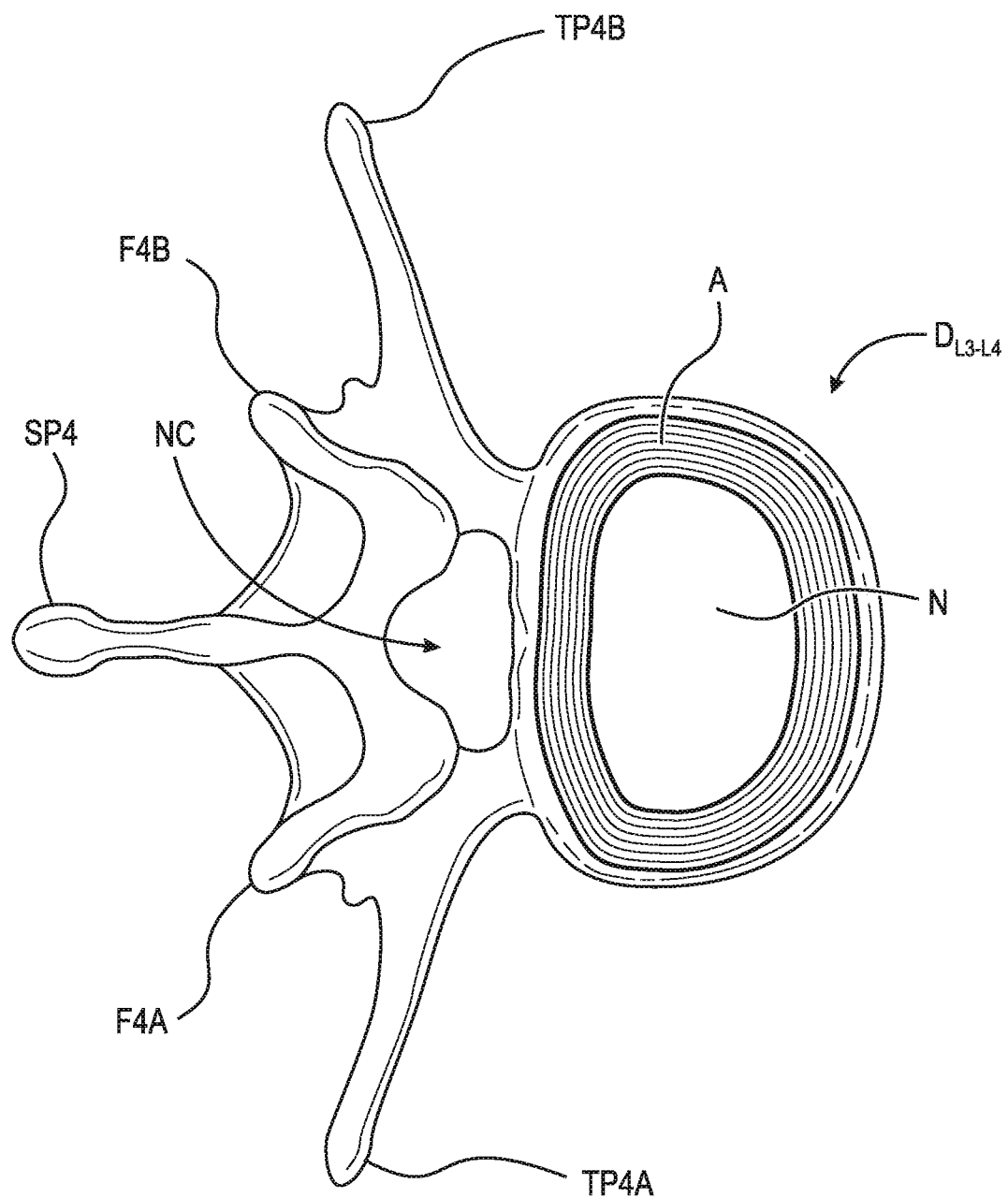
FIG. 4 is a top view of a section of the spinal column, taken generally along line 4-4 in FIG. 3.
Figure 5:
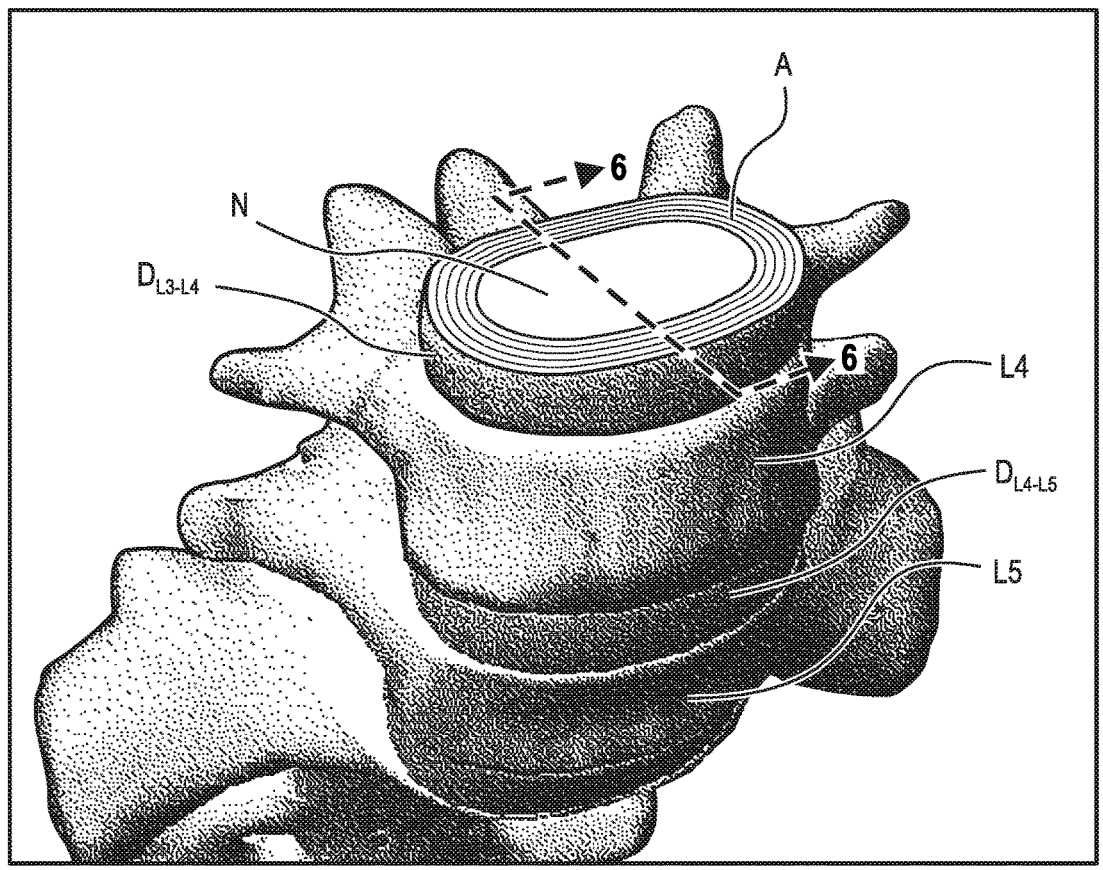
FIG. 5 is an enlarged anterior perspective view of the spinal column shown in FIG. 2, except with the top vertebra and all other structure above the top vertebra removed.
Figure 6:
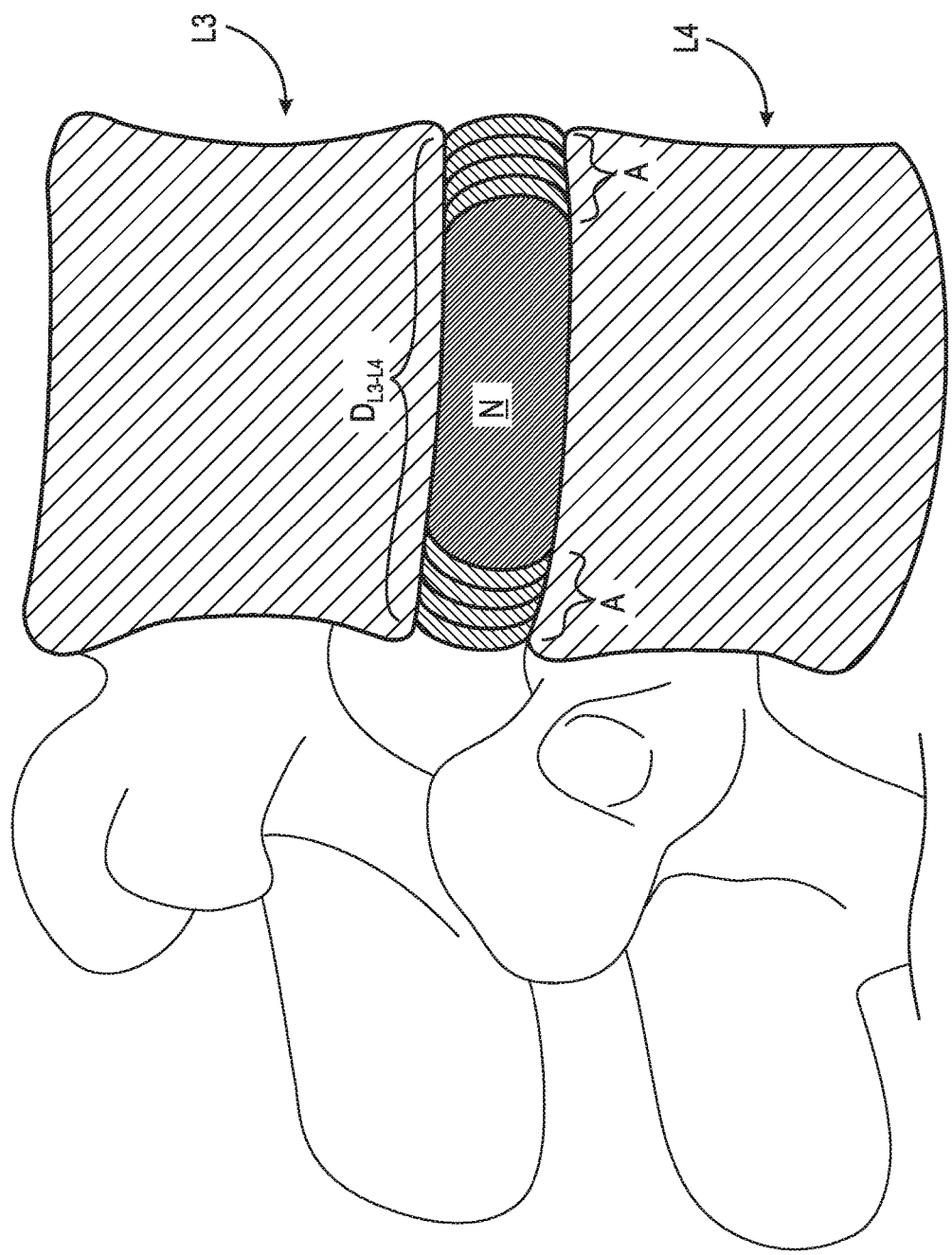
FIG. 6 is a partial cross-sectional view of the top and bottom vertebrae and disc, taken generally along line 6-6 in FIG. 5.
Figures 7A, 7B:
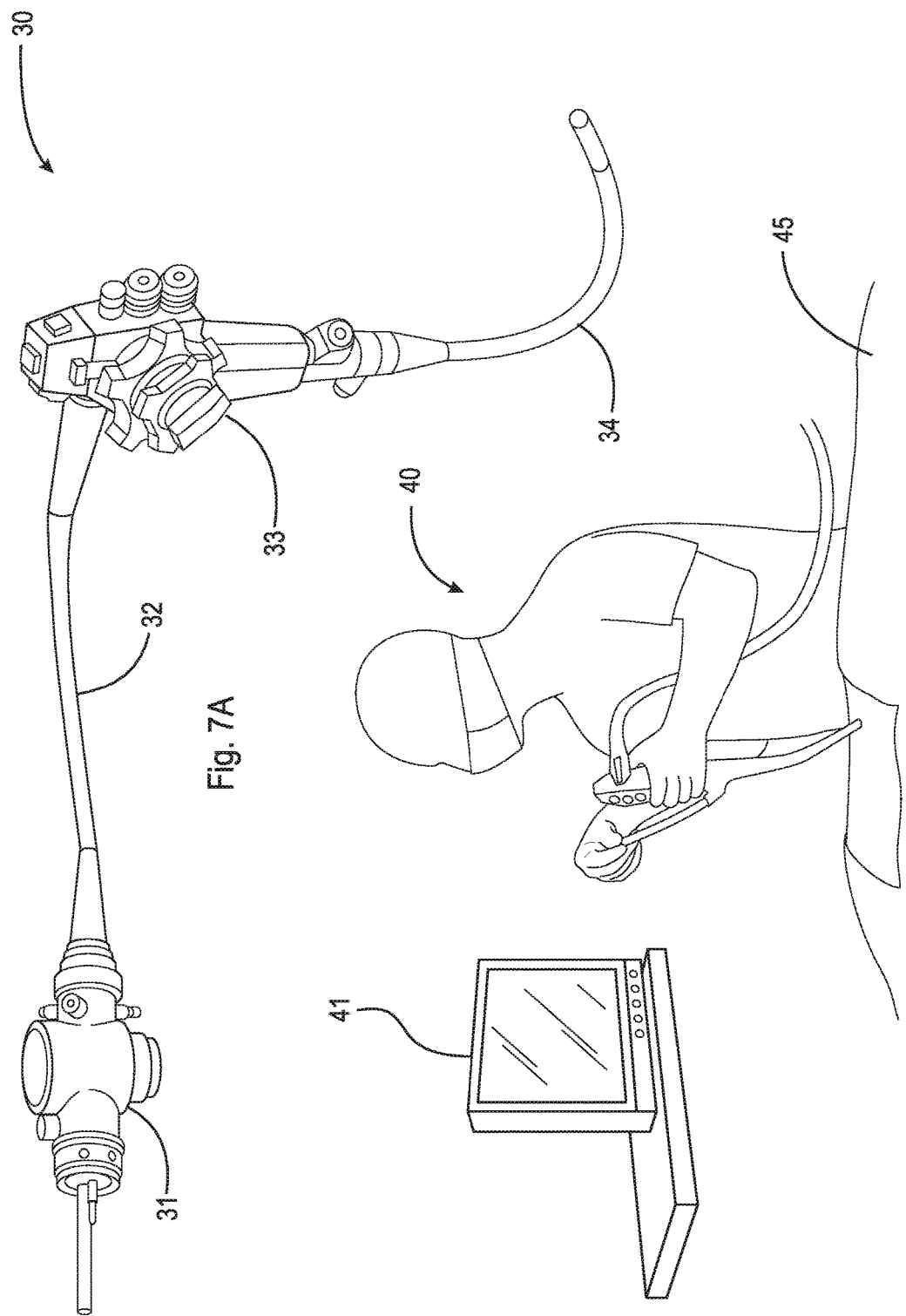
FIG. 7A is a view of a typical endoscope.
FIG. 7B illustrates use of the endoscope shown in FIG. 7A by a surgeon performing a discectomy (diskectomy)

Adverting now to the figures, and as described previously, FIGS. 1-6 depict various parts and sections of spinal anatomy, and FIGS. 7A and 7B depict a typical endoscope for use by a surgeon on a patient.

Figure 8:
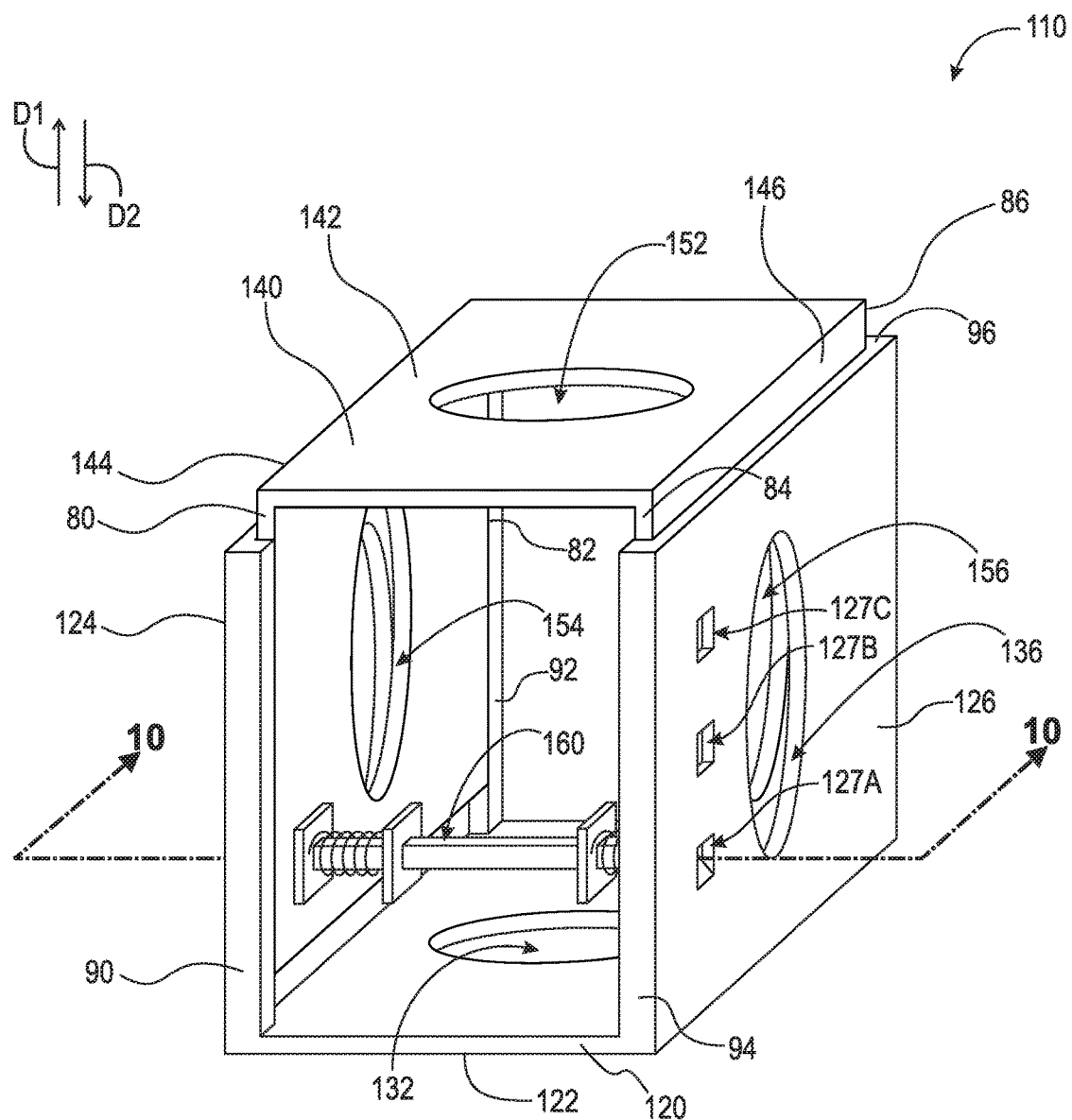
FIG. 8 is a top perspective view of an expandable intervertebral implant, in a collapsed state.
Figure 9:
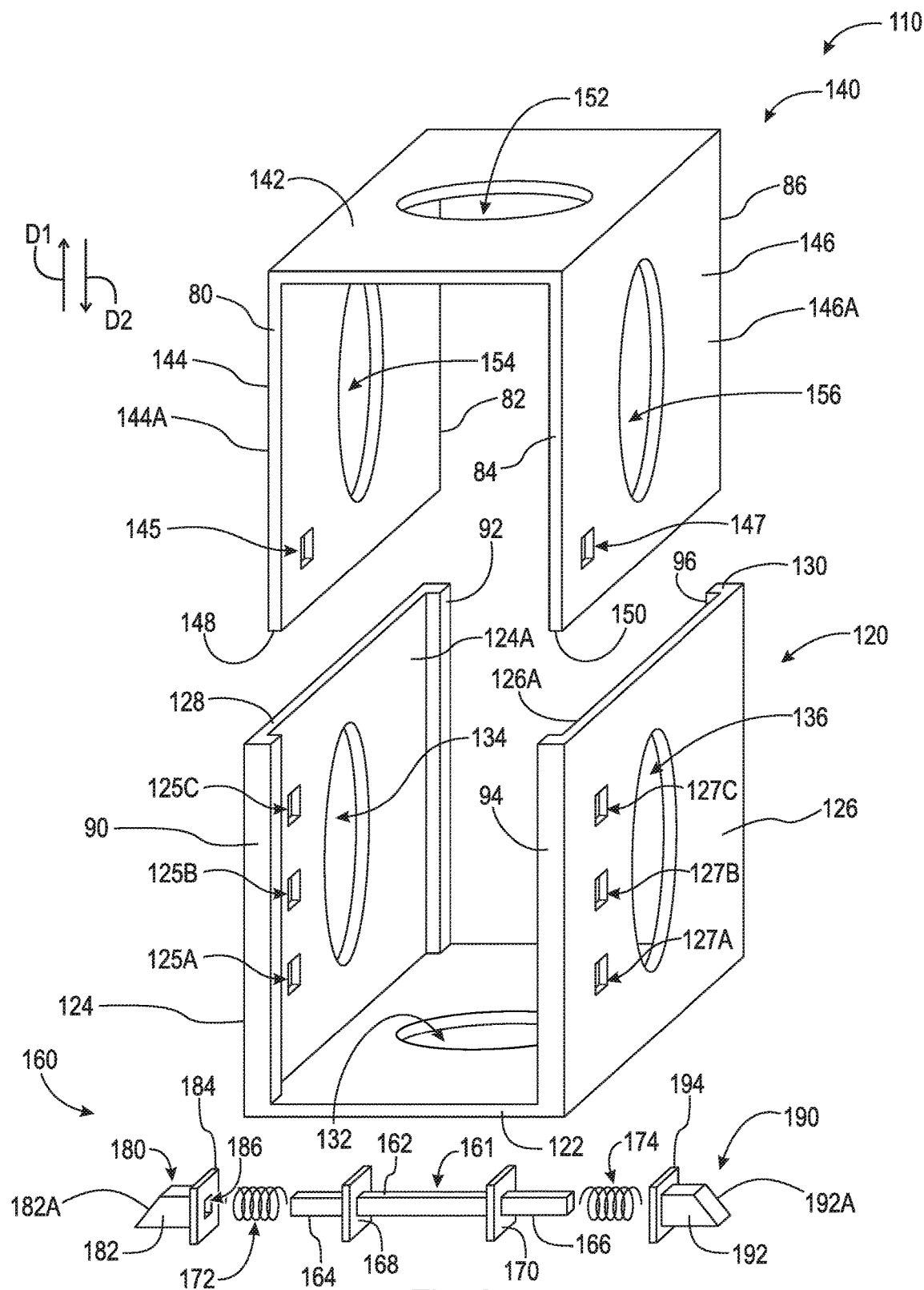
FIG. 9 is an exploded view of the expandable intervertebral implant shown in FIG. 8.

FIG. 8 is a top perspective view of expandable intervertebral implant 110, in a collapsed state. FIG. 9 is an exploded view of expandable intervertebral implant 110. Expandable intervertebral implant 110 generally comprises inferior component 120, superior component 140, and locking pin assembly 160.

Inferior component 120 comprises plate 122, plate 124, and plate 126. Plate 122 is arranged to at least partially abut against a vertebra and comprises aperture 132.

Plate 124 is connected and arranged substantially perpendicular to plate 122. Plate 124 comprises surface 124A, end 128, aperture 134, and a plurality of locking apertures 125A-C. End 128 is directed away from plate 122. Aperture 134 extends completely through plate 124. In the embodiment shown, locking apertures 125A-C extend completely through plate 124 and are preferably arranged along a substantially vertical linear line. In an example embodiment, locking apertures 125A-C may extend partially through plate 124 from surface 124A. It should be appreciated that plate 124 may comprise any number of locking apertures in any arrangement suitable for expanding expandable intervertebral implant 110 to a desired a length between adjacent vertebrae. In the embodiment shown, locking apertures 125A-C comprise a square-shaped geometry. However, it should be appreciated that locking apertures 125A-C may comprise any suitable geometric shape (e.g., circular, ovular, triangular, trapezoidal, etc.) such that superior component 140 may be locked with inferior component 120 at a desired length using locking pin assembly 160. As shown in FIG. 8, plate 124 may further comprise flanges 90 and 92 extending from surface 124A. Flanges 90 and 92 provide a track for superior component 140 as will be discussed in greater detail below. In an example embodiment, plate 124 does not comprise flanges 90 and 92. In an example embodiment, plate 124 is curvilinear such that when implant 110 is expanded/contracted, inferior component 120 and superior component 140 move in a non-linear path.

Plate 126 is connected and arranged substantially perpendicular to plate 122. Plate 126 comprises surface 126A, end 130, aperture 136, and a plurality of locking apertures 127A-C. End 130 is directed away from plate 122. Surfaces 124A and 126A are directed toward each other. Aperture 136 extends completely through plate 126. In the embodiment shown, locking apertures 127A-C extend completely through plate 126 and are preferably arranged along a substantially vertical linear line. In an example embodiment, locking apertures 127A-C may extend partially through plate 126 from surface 126A. It should be appreciated that plate 126 may comprise any number of locking apertures in any arrangement suitable for expanding expandable intervertebral implant 110 to a desired a length between adjacent vertebrae. Moreover, locking apertures 125A-C are axially aligned with locking apertures 127A-C. In an example embodiment, locking apertures 125A-C are not aligned with locking apertures 127A-C. In the embodiment shown, locking apertures 127A-C comprise a square-shaped geometry. However, it should be appreciated that locking apertures 127A-C may comprise any suitable geometric shape (e.g., circular, ovular, triangular, trapezoidal, etc.) such that superior component 140 may be locked with inferior component 120 at a desired length using locking pin assembly 160. As shown in FIG. 8, plate 126 may further comprise flanges 94 and 96 extending from surface 126A. Flanges 94 and 96 provide a track for superior component 140 as will be discussed in greater detail below. In an example embodiment, plate 126 does not comprise flanges 94 and 96. In an example embodiment, plate 126 is curvilinear such that when implant 110 is expanded/contracted, inferior component 120 and superior component 140 move in a non-linear path.

Superior component 140 comprises plate 142, plate 144, and plate 146. Plate 142 is arranged to at least partially abut against a vertebra and comprises aperture 152.

Plate 144 is connected and arranged substantially perpendicular to plate 142. Plate 144 comprises surface 144A, end 148, edges 80 and 82, aperture 154, and locking aperture 145. End 148 is directed away from plate 142. Aperture 154 extends completely through plate 144. Locking aperture 145 extends completely through plate 144. When assembled, locking aperture 145 is arranged to align with any of locking apertures 125A-C. In the embodiment shown, locking aperture 145 comprises a square-shaped geometry. However, it should be appreciated that locking aperture 145 may comprise any suitable geometric shape (e.g., circular, ovular, triangular, trapezoidal, etc.) such that superior component 140 may be locked with inferior component 120 at a desired length using locking pin assembly 160. Plate 144 is arranged to slidingly engage plate 124. Specifically, edges 80 and 82 are at least partially enclosed by flanges 90 and 92, respectively, which maintains level expansion and retraction of expandable intervertebral implant 110. In an example embodiment, edges 80 and 82 at least partially abut against flanges 90 and 92, respectively. In an example embodiment, plate 144 is curvilinear such that when implant 110 is expanded/contracted, inferior component 120 and superior component 140 move in a non-linear path.

Plate 146 is connected and arranged substantially perpendicular to plate 142. Plate 146 comprises surface 146A, end 150, edges 84 and 86, aperture 156, and locking aperture 147. End 150 is directed away from plate 142. Surfaces 144A and 146A are directed away from each other. Aperture 156 extends completely through plate 146. Locking aperture 147 extends completely through plate 146. When assembled, locking aperture 147 is arranged to align with any of locking apertures 127A-C. In the embodiment shown, locking aperture 147 comprises a square-shaped geometry. However, it should be appreciated that locking aperture 147 may comprise any suitable geometric shape (e.g., circular, ovular, triangular, trapezoidal, etc.) such that superior component 140 may be locked with inferior component 120 at a desired length using locking pin assembly 160. Plate 146 is arranged to slidingly engage plate 126. Specifically, edges 84 and 86 are at least partially enclosed by flanges 94 and 96, respectively, which maintains level expansion and retraction of expandable intervertebral implant 110. In an example embodiment, edges 84 and 86 at least partially abut against flanges 94 and 96, respectively. In an example embodiment, plate 146 is curvilinear such that when implant 110 is expanded/contracted, inferior component 120 and superior component 140 move in a non-linear path.

When inferior component 120 and superior component 140 are assembled, plates 144 and 146 are arranged axially between plates 124 and 126. Ends 148 and 150 are directed toward plate 122 and ends 128 and 130 are directed toward plate 142. Surface 144A is directed toward surface 124A and surface 146A is directed toward surface 126A. Edges 80 and 82 are arranged proximate flanges 90 and 92, respectively, and edges 84 and 86 are arranged proximate flanges 94 and 96, respectively. In an example embodiment, superior component 140 slidingly fits within inferior component 120. Plates 144 and 124 substantially abut such that surface 144A slides against surface 124A and edges 80 and 82 slide against flanges 90 and 92, respectively. Plates 146 and 126 substantially abut such that surface 146A slides against surface 126A and edges 84 and 86 slide against flanges 94 and 96, respectively. In an example embodiment, plate 124 may further comprise flanges extending from surface 124A on one or both sides adjacent to end 128 (not shown). In an example embodiment, plate 126 may further comprise flanges extending from surface 126A on one or both sides adjacent to end 130 (not shown). When bone material is packed into expandable intervertebral implant 110, apertures (or openings) 132, 134, 136, 152, 154, and 156 are arranged to allow bony growth material around and within expandable intervertebral implant 110. In an example embodiment, bony growth and permanent fixation may be achieved with hardenable materials such as bone putty or methyl methylacrylate (MMA) as is known to those having ordinary skill in the art. In the embodiment shown, apertures 132, 134, 136, 152, 154, and 156 are circular or ovular. However, it should be appreciated that apertures 132, 134, 136, 152, 154, and 156 may comprise any geometry suitable for allowing bone material to create bony growth and fusion.

Locking pin assembly 160 generally comprises shaft 161, springs 172 and 174, and engaging members 180 and 190. Shaft 161 comprises middle portion 162, end 164, end 166, flange 168, and flange 170. Flange 168 is arranged between end 164 and middle portion 162, and flange 170 is arranged between end 166 and middle portion 162. In the embodiment shown, middle portion 162 comprises a square-shaped cross-sectional geometry. However, it should be appreciated that middle portion 162 may comprise any suitable geometric shape (e.g., circular, ovular, triangular, trapezoidal, etc.). Spring 172 is arranged around end 164 and axially between flange 168 and flange 184. Spring 174 is arranged around end 166 and axially between flange 170 and flange 194.

Engaging member 180 comprises flange 184 and pin 182 extending axially therefrom. Aperture 186 extends through flange 184 and at least partially through pin 182. Pin 182 comprises beveled surface 182A. In an example embodiment, pin 182 does not comprise a beveled surface. In the embodiment shown, pin 182 comprises a square-shaped cross-sectional geometry to match that of locking apertures 145 and 125A-C. However, it should be appreciated that pin 182 may comprise any suitable geometric shape (e.g., circular, ovular, triangular, trapezoidal, etc.) such that superior component 140 may be locked with inferior component 120 at a desired length using locking pin assembly 160. The geometries of pin 182 and locking apertures 145 and 125A-C should match. End 164 is arranged to slidingly engage aperture 186, and thus their geometries and sizes should be designed accordingly.

Engaging member 190 comprises flange 194 and pin 192 extending axially therefrom. Aperture 196 (not shown) extends through flange 194 and at least partially through pin 192. Pin 192 comprises beveled surface 192A. In an example embodiment, pin 192 does not comprise a beveled surface. In the embodiment shown, pin 192 comprises a square-shaped cross-sectional geometry to match that of locking apertures 147 and 127A-C. However, it should be appreciated that pin 192 may comprise any suitable geometric shape (e.g., circular, ovular, triangular, trapezoidal, etc.) such that superior component 140 may be locked with inferior component 120 at a desired length using locking pin assembly 160. The geometries of pin 192 and locking apertures 147 and 127A-C should match. End 166 is arranged to slidingly engage aperture 196, and thus their geometries and sizes should be designed accordingly.

In the embodiment shown, flanges 168, 170, 184, and 194 comprises a square-shaped cross-sectional geometry. However, it should be appreciated that flanges 168, 170, 184, and 194 may comprise any suitable geometric shape (e.g., circular, ovular, triangular, trapezoidal, etc.). When expandable intervertebral implant 110 is assembled, a tool (not shown) is used to displace flanges 184 and 194 axially inward (i.e., toward each other), thereby compressing springs 172 and 174 and disengaging pins 182 and 192 from locking apertures 125A-C and 127A-C, respectively. This allows superior component 140 to be move relative to inferior component. To lock superior component 140 with inferior component 120, the tool is used to displace flanges 184 and 194 axially outward (i.e., away from each other), thereby engaging pins 182 and 192 with locking apertures 125A-C and 127A-C, respectively. This process is discussed in greater detail below with respect to FIGS. 10A-D.

Figure 10A:
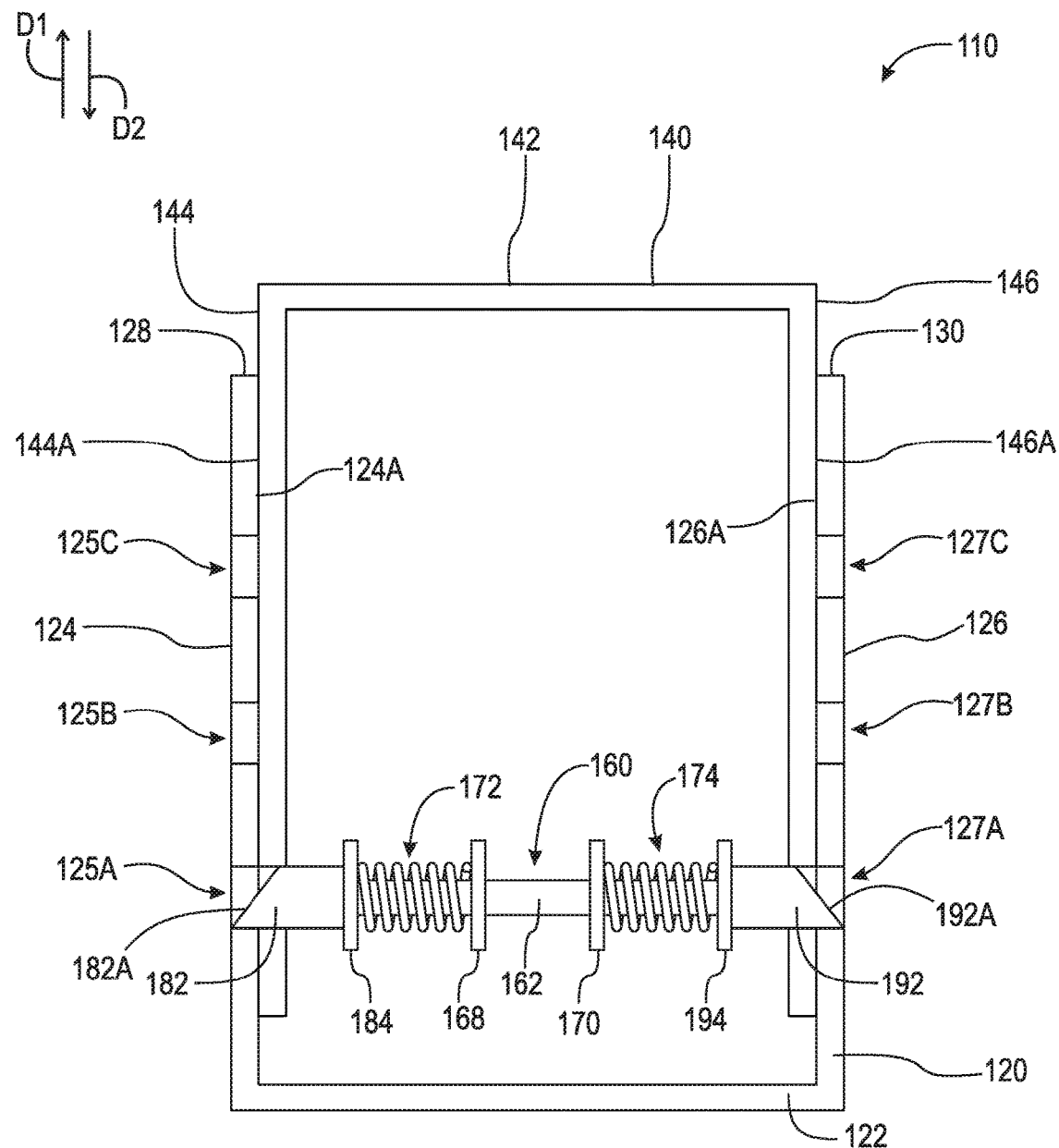
FIG. 10A is a cross-sectional view of the expandable intervertebral implant shown in FIG. 8 taken generally along line 10-10.

FIG. 10A is a cross-sectional view of expandable intervertebral implant 110 taken generally along line 10-10 in FIG. 8. FIG. 10A shows expandable intervertebral implant 110 in a collapsed state, wherein locking pin assembly 160 is in a neutral position. When locking pin assembly 160 is in the neutral position (i.e., no force is asserted on flanges 184 or 194), springs 172 and 174 are arranged to position pins 182 and 192 partially within locking apertures 125A-C and 127A-C, respectively. In the neutral position, superior component 140 may be displaced in direction D1 relative to inferior component 120, thus expanding expandable intervertebral implant 110 but cannot be displaced in direction D2 relative to inferior component. This restricted movement is caused by beveled surfaces 182A and 192A, which act as a ratchet mechanism similar to that in a jack stand.

Figure 10B:
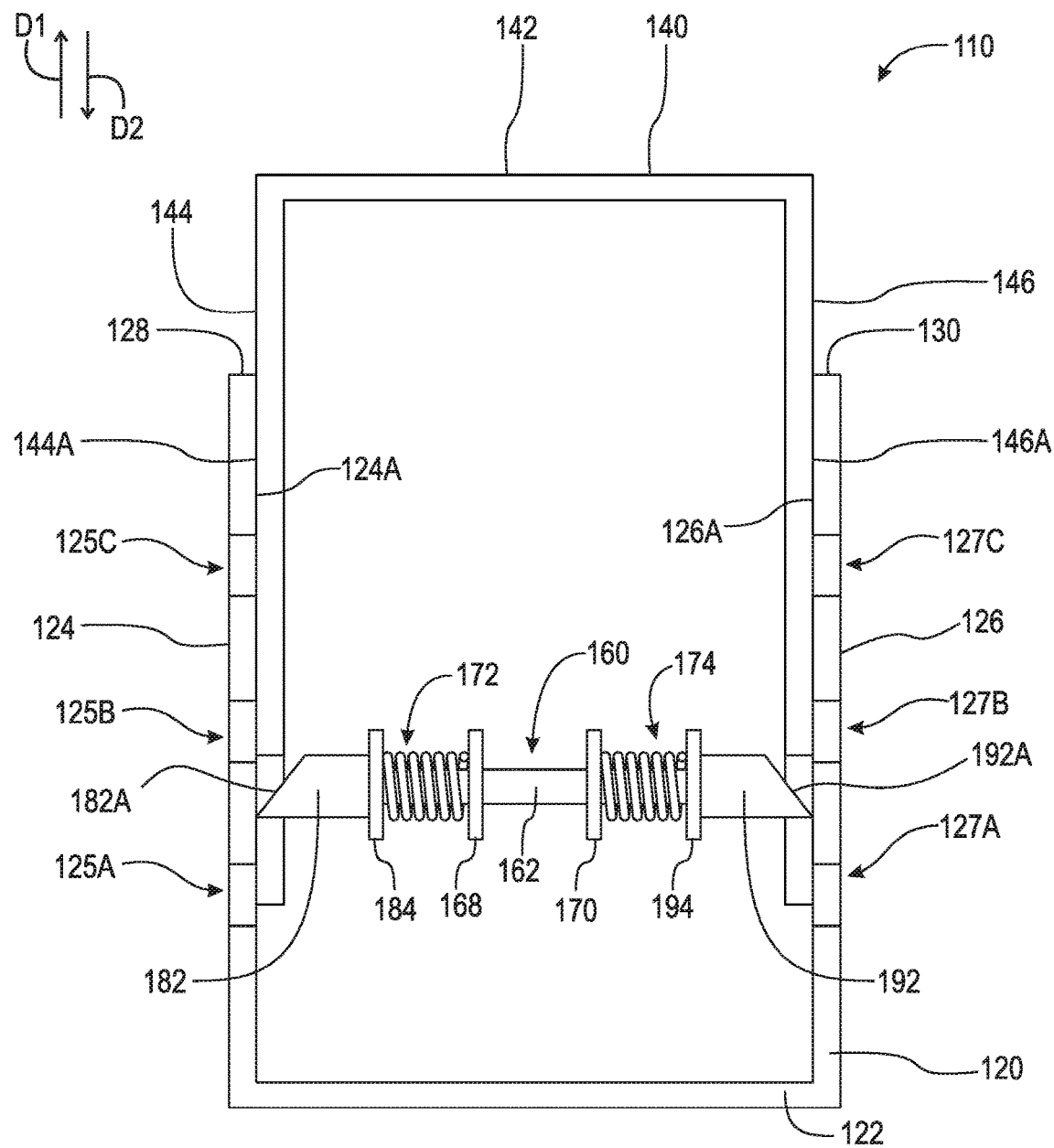
FIG. 10B is cross-sectional view of the expandable intervertebral implant shown in FIG. 10A in a partially expanded state.

FIG. 10B is cross-sectional view of expandable intervertebral implant 110 in a partially expanded state. FIG. 10B shows expandable intervertebral implant 110 in a partially expanded state, wherein locking pin assembly 160 is in a compressed position. When superior component 140 is displaced in direction D1 relative to inferior component 120, beveled surfaces 182A and 192A cause pins 182 and 192 to displace axially inward (i.e., toward each other) thereby disengaging pins 182 and 192 from locking apertures 125A-C and 127A-C, respectively. Alternatively, a tool could be used to engage flanges 184 and 194 and displace pins 182 and 192 axially inward. In this situation, pins 182 and 192 would remain fully disengaged from locking apertures 125A-C and 127A-C, respectively. The tool would be used to compress expandable intervertebral implant 110 such that superior component 140 moves in direction D2 relative to inferior component 120. It should be appreciated that the same tool may be used to engage flanges 184 and 194 as discussed above and also expand expandable intervertebral implant 110. In an example embodiment, two separate tools may be used, one to engage flanges 184 and 194 as discussed above and the other to expand expandable intervertebral implant 110.

Figure 10C:
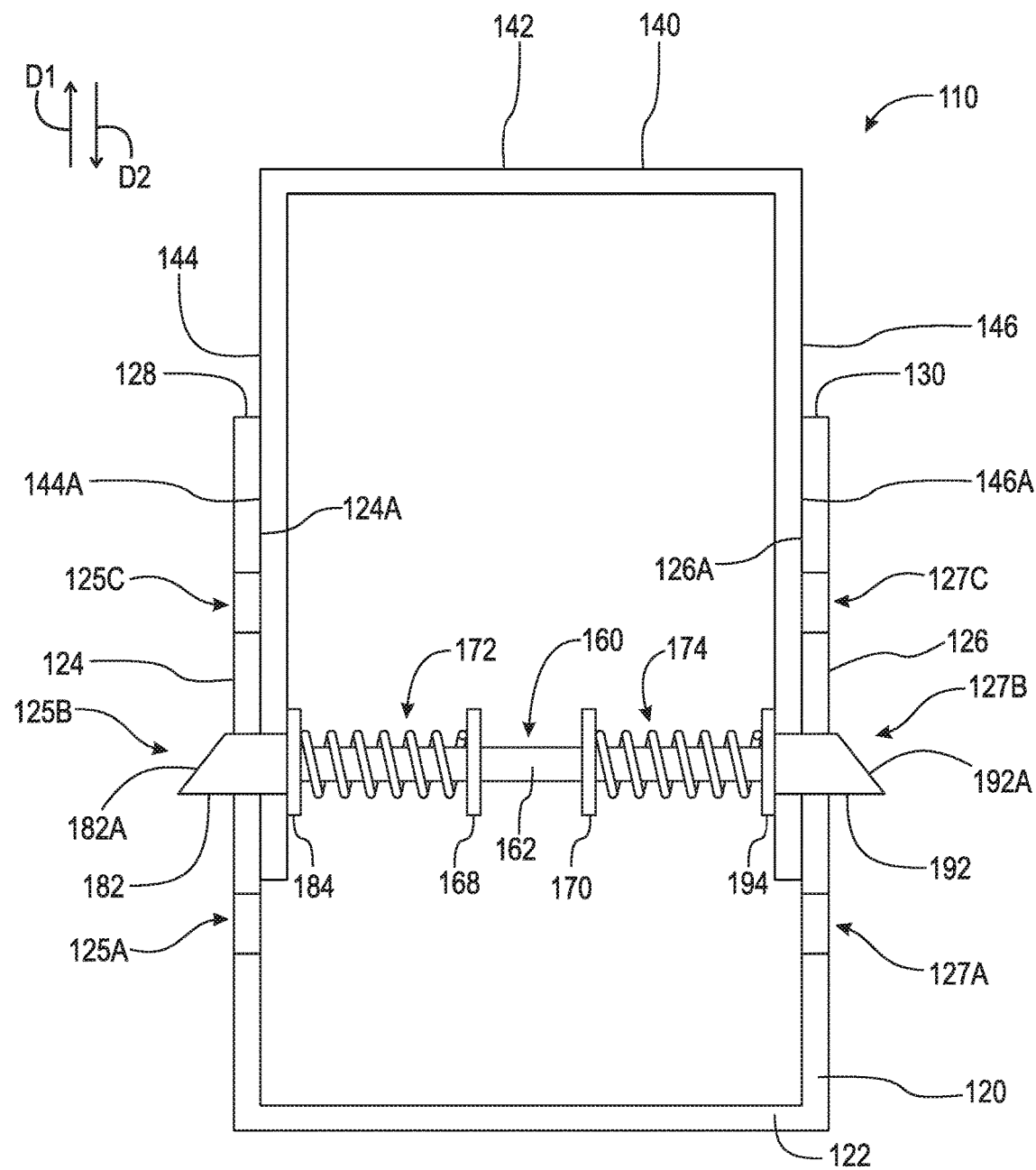
FIG. 10C is cross-sectional view of the expandable intervertebral implant shown in FIG. 10A in a partially expanded state.

FIG. 10C is cross-sectional view of expandable intervertebral implant 110 in a partially expanded state. FIG. 10C shows expandable intervertebral implant 110 in a partially expanded state, wherein locking pin assembly 160 is in a locked position. When expandable intervertebral implant 110 is expanded to the desired length, pins 182 and 192 are displaced axially outward (i.e., away from each other) to engage locking apertures 125A-C and 127A-C, respectively. In the locked position, beveled surfaces 182A and 192A are arranged completely on the axially outer side of plates 124 and 126, respectively. This prevents superior component 140 from displacing in directions D1 and D2 with respect to inferior component 120. In an example embodiment, in the locked position, flanges 184 and 194 abut against plates 144 and 146, respectively. Pins 182 and 192 can be moved to the locked position using the flange engaging tool discussed above or any other suitable method. It should be appreciated, that in an example embodiment, springs 172 and 174 can be arranged to force pins 182 and 192 to the locked position when aligned with locking apertures 125A-C and 127A-C, respectively.

Figure 10D:
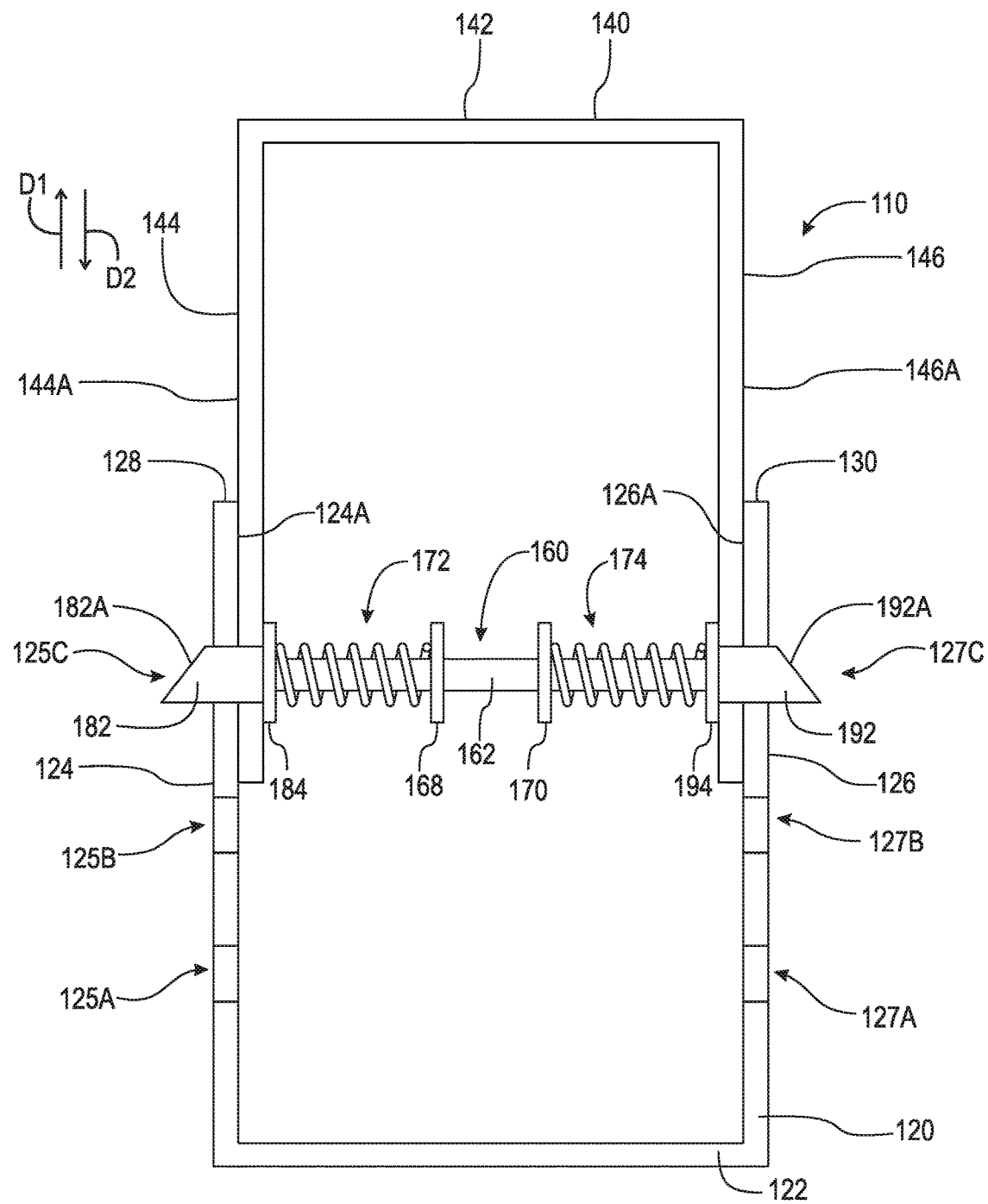
FIG. 10D is cross-sectional view of the expandable intervertebral implant shown in FIG. 10A in a fully expanded state.

FIG. 10D is cross-sectional view of expandable intervertebral implant 110 in a fully expanded state. FIG. 10D shows expandable intervertebral implant 110 in a fully expanded state, wherein locking pin assembly 160 is in a locked position. When expandable intervertebral implant 110 is expanded to the fully expanded length, pins 182 and 192 are displaced axially outward (i.e., away from each other) to engage locking apertures 125C and 127C, respectively. In the locked position, beveled surfaces 182A and 192A are arranged completely on the axially outer side of plates 124 and 126, respectively. This prevents superior component 140 from displacing in directions D1 and D2 with respect to inferior component 120. In an example embodiment, in the locked position, flanges 184 and 194 abut against plates 144 and 146, respectively. Pins 182 and 192 can be moved to the locked position using the flange engaging tool discussed above or any other suitable method. It should be appreciated, that in an example embodiment, springs 172 and 174 can be arranged to force pins 182 and 192 to the locked position when aligned with locking apertures 125A-C and 127A-C, respectively.

Figure 11:
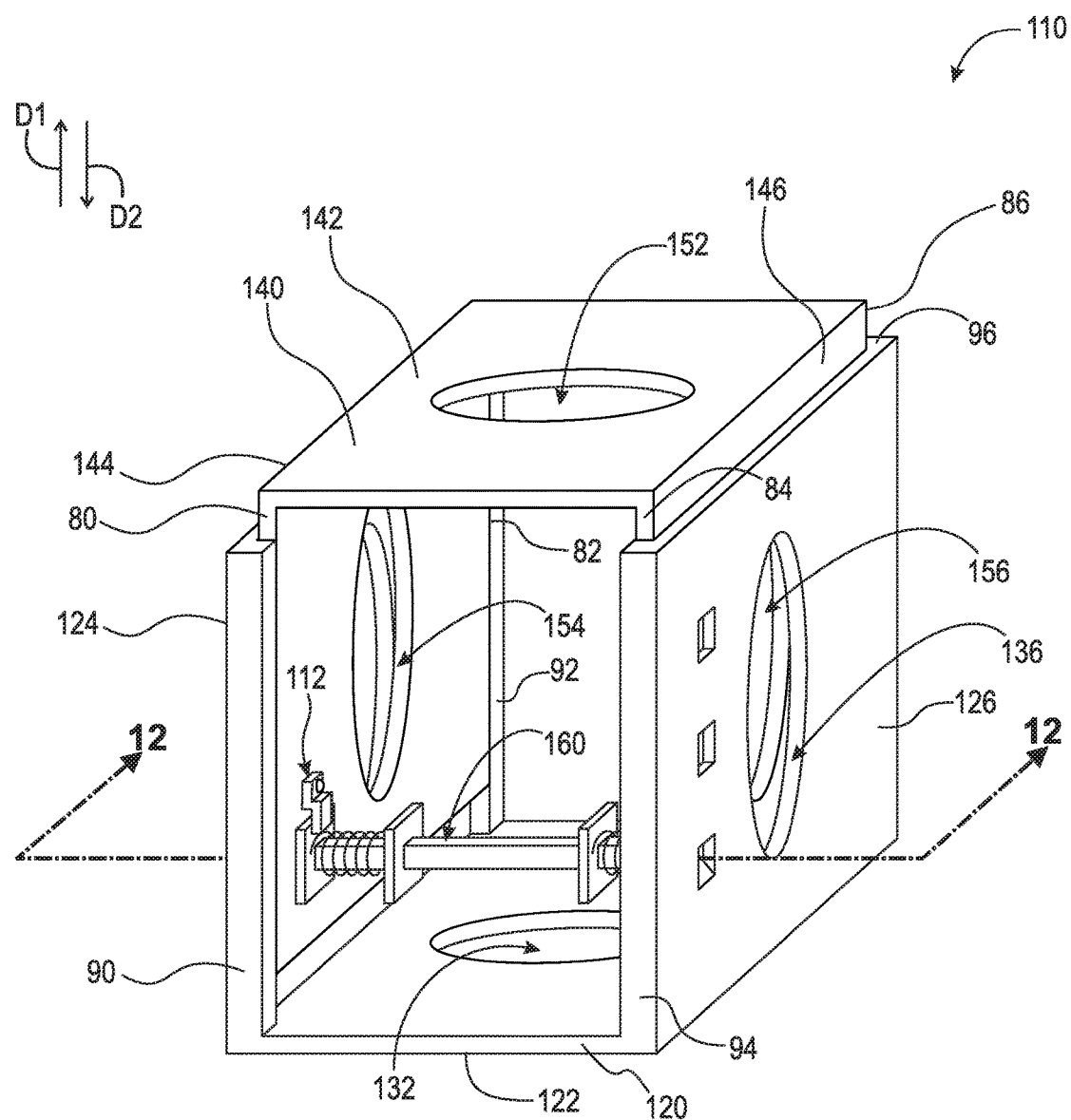
FIG. 11 is a top perspective view of an expandable intervertebral implant.
Figure 13:
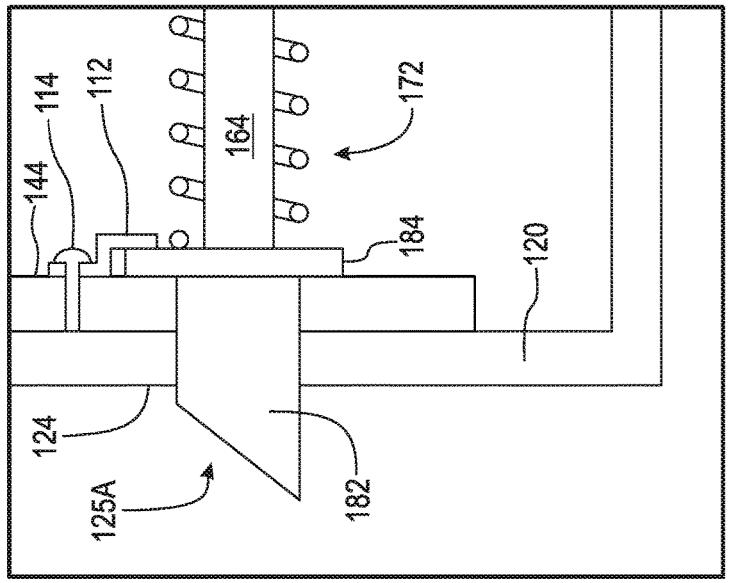
FIG. 13 is a cross-sectional view of the expandable intervertebral implant shown in FIG. 12 taken generally of detail 13.
Figure 12:
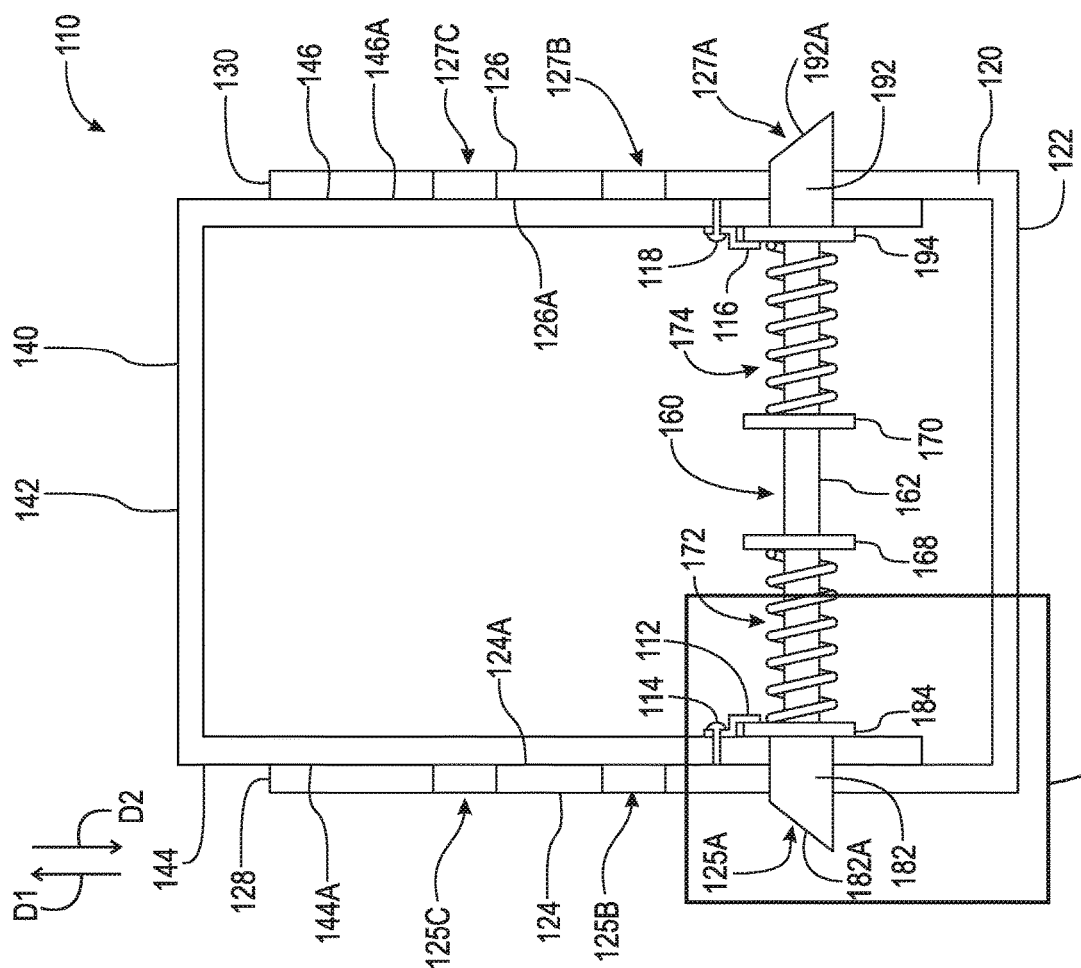
FIG. 12 is a cross-sectional view of the expandable intervertebral implant shown in FIG. 11 taken generally along line 12-12.

FIG. 11 is a top perspective view of expandable intervertebral implant 110. FIG. 12 is a cross-sectional view of the expandable intervertebral implant 110 taken generally along line 12-12 in FIG. 11. FIG. 13 is a cross-sectional view of the expandable intervertebral implant 110 taken generally of detail 13 in FIG. 12. In the embodiment shown, superior component 140 further comprises locking plates 112 and 118. Locking plate 112 is rotatably secured to plate 144 using fastener 114. Fastener 114 may be a screw, bolt, rivet, pin, or any other device suitably for rotatably connecting locking plate 112 to plate 144. Locking plate 112 is arranged vertically above locking aperture 145 to rotate and axially lock flange 184 against plate 144. Locking plate 116 is rotatably secured to plate 146 using fastener 118. Fastener 118 may be a screw, bolt, rivet, pin, or any other device suitably for rotatably connecting locking plate 116 to plate 146. Locking plate 116 is arranged vertically above locking aperture 147 to rotate and axially lock flange 194 against plate 146. It should be appreciated that the present disclosure is not limited to the use of a locking plate and that any suitable locking mechanism or locking mechanisms may be used.

Figure 14:
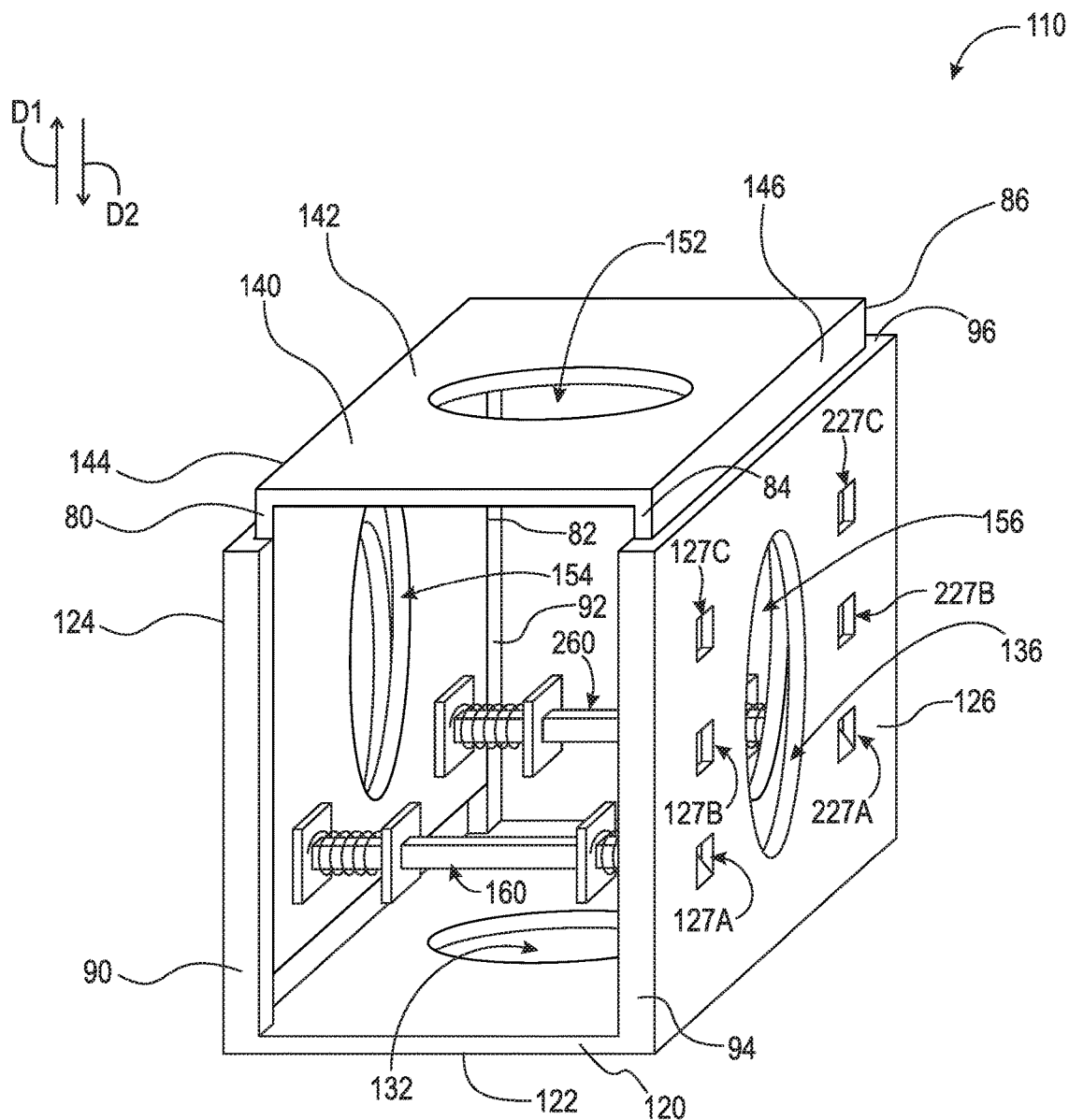
FIG. 14 is a top perspective view of an expandable intervertebral implant.

FIG. 14 is a top perspective view of expandable intervertebral implant 110. In the embodiment shown, expandable intervertebral implant 110 comprises an additional pin locking assembly 260. Thus, in addition to the embodiment shown in FIG. 8, inferior component 120 further comprises locking apertures 225A-C (not shown) and 227A-C. Superior component 140 further comprises locking aperture 245 (not shown) and 247 (not shown). Locking pin assembly 260 is substantially the same as locking pin assembly 160 and engages locking apertures 225A-C, 227A-C, 245, and 247.

Figure 15:
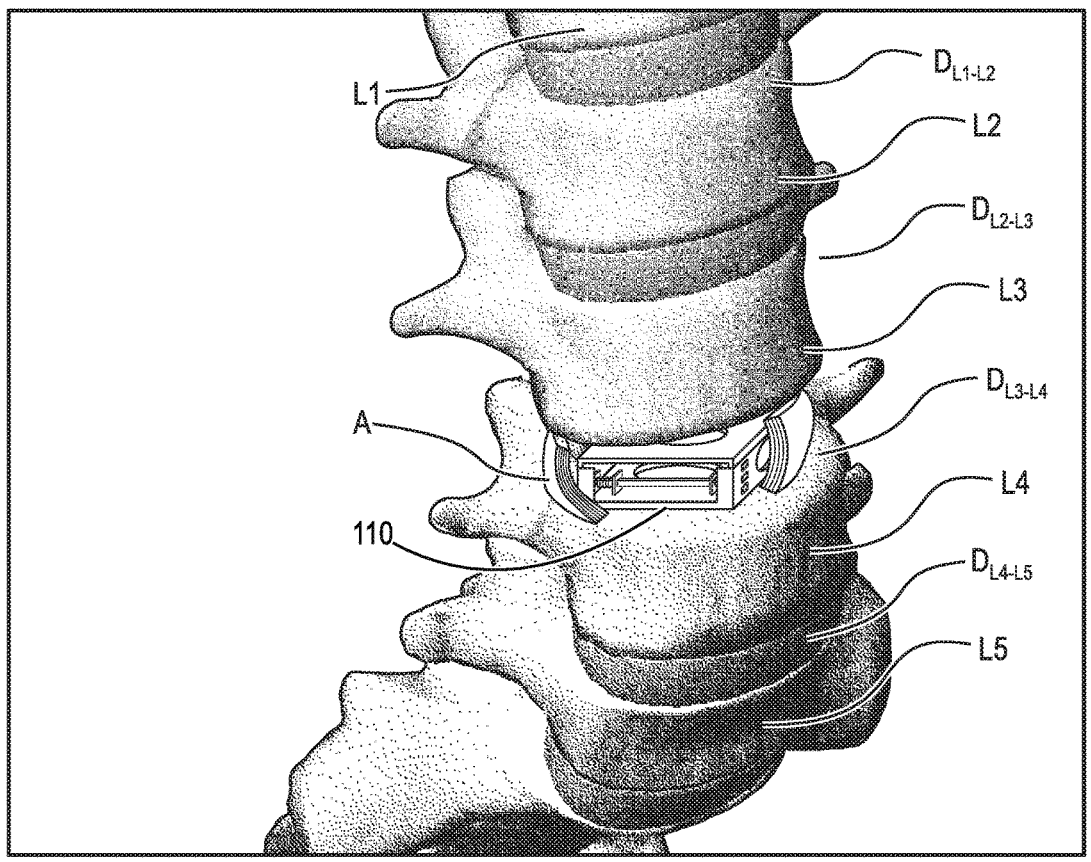
FIG. 15 is an anterior perspective view of a spinal column including the expandable intervertebral implant shown in FIG. 8.

FIG. 15 is an anterior perspective view of a spinal column including expandable intervertebral implant 110. Expandable intervertebral implant 110 is inserted into the spinal column between, for example, the L3 and L4 vertebrae, or where disc $D_{L3-L4}$ should be. In an example embodiment, expandable intervertebral implant 110 may be secured to the vertebrae, for example, by fasteners such as screws, anchors, bolts, etc., or any other suitable fastening mechanism, including adhesives. Expandable intervertebral implant 110 is then vertically expanded until the desired height is reached. Specifically, superior component 140 is displaced vertically upward relative to inferior component 120 using an expansion tool. When the desired length is acquired, the engaging members are locked in their respective locking apertures. Expandable intervertebral implant 110 is then filled with fusion material and left in situ. It should be appreciated that expandable intervertebral implant 110 can be adjusted to a suitable length prior to inserting expandable intervertebral implant 110 into the spinal column.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
30 Endoscope
31 Light guide connector
32 Light guide tube
33 Control body
34 Insertion tube
40 Surgeon
41 Monitor
42 Patient
80 Edge
82 Edge
84 Edge
86 Edge
90 Flange
92 Flange
94 Flange
96 Flange
110 Expandable intervertebral implant
112 Locking plate
114 Fastener
116 Locking plate
118 Fastener
120 Inferior component
122 Plate
124 Plate
124A Surface
125A Locking aperture
125B Locking aperture
125C Locking aperture
126 Plate
126A Surface
127A Locking aperture
127B Locking aperture
127C Locking aperture
128 End
130 End
132 Aperture
134 Aperture
136 Aperture
140 Superior component
142 Plate
144 Plate
144A Surface
145 Locking aperture
146 Plate
146A Surface
147 Locking aperture
148 End
150 End
152 Aperture
154 Aperture
156 Aperture
160 Locking pin assembly
161 Shaft
162 Middle portion
164 End
166 End
168 Flange
170 Flange
172 Spring
174 Spring
180 Engaging member
182 Pin
182A Beveled surface
184 Flange
186 Aperture
190 Engaging member
192 Pin 192A Beveled surface
194 Flange
196 Aperture (not shown)
225A Locking aperture (not shown)
225B Locking aperture (not shown)
225C Locking aperture (not shown)
227A Locking aperture
227B Locking aperture
227C Locking aperture
260 Locking pin assembly
D1 Direction
D2 Direction

What is claimed is:

1. An expandable intervertebral implant, comprising:
an inferior component, including:
 a first plate;
 a second plate connected to the first plate and comprising a first plurality of locking apertures; and,
 a third plate connected to the first plate and comprising a second plurality of locking apertures, wherein the second and third plates are fixedly secured to the first plate;
a superior component slidingly engaged with the inferior component, including:
 a fourth plate;
 a fifth plate connected to the fourth plate and comprising a third locking aperture; and,
 a sixth plate connected to the fourth plate and comprising a fourth locking aperture; and,
a locking pin assembly:
 arranged at least partially in the third and fourth locking apertures; and,
 operatively arranged to engage the first and second pluralities of locking apertures to lock the expandable intervertebral implant.

2. The expandable intervertebral implant as recited in claim 1, wherein:
the second and third plates are arranged substantially perpendicular to the first plate; and,
the fifth and sixth plates are arranged substantially perpendicular to the third plate.

3. The expandable intervertebral implant as recited in claim 1, wherein:
the second plate includes at least one first vertical flange; and,
the third plate includes at least one second vertical flange.

4. The expandable intervertebral implant as recited in claim 1, wherein the locking pin assembly comprises:
a shaft including a first end and a second end;
a first spring arranged on the first end;
a second spring arranged on the second end;
a first engaging member slidingly engaged with the first end; and,
a second engaging member slidingly engaged with the second end.

5. The expandable intervertebral implant as recited in claim 4, wherein:
the first engaging member is arranged in the third locking aperture and is biased toward the first plurality of locking apertures by the first spring; and,
the second engaging member is arranged in the fourth locking aperture and is biased toward the second plurality of locking apertures by the second spring.

6. The expandable intervertebral implant as recited in claim 5, wherein:
the first engaging member comprises a first flange engaged with the first spring and a first pin extending from the first flange; and,
the second engaging member comprises a second flange engaged with the second spring and a second pin extending from the second flange.

7. The expandable intervertebral implant as recited in claim 6, wherein:
the first pin includes a first beveled surface; and,
the second pin includes a second beveled surface.

8. The expandable intervertebral implant as recited in claim 7, wherein when the locking pin assembly is in a neutral state:
the first beveled surface is at least partially engaged with one of the first plurality of locking apertures;
the second beveled surface is at least partially engaged with one of the second plurality of locking apertures; and,
the superior component is capable of being displaced in a first direction relative to the inferior component.

9. The expandable intervertebral implant as recited in claim 8, wherein when the locking pin assembly is in a compressed state:
the first beveled surface is not engaged with any of the first plurality of locking apertures;
the second beveled surface is not engaged with any of the second plurality of locking apertures; and,
the superior component is capable of being displaced in the first direction and a second direction, opposite of the first direction, relative to the inferior component.

10. The expandable intervertebral implant as recited in claim 9, wherein when the locking pin assembly is in a locked state:
the first pin is fully engaged with one of the first plurality of locking apertures;
the second pin is fully engaged with one of the second plurality of locking apertures; and,
the superior component is not capable of being displaced in the first direction or the second direction relative to the inferior component.

11. The expandable intervertebral implant as recited in claim 1, wherein the first and second pluralities of locking apertures extend completely through the second and third plates, respectively.

12. The expandable intervertebral implant as recited in claim 1, wherein the first and second pluralities of locking apertures extend only partially through the second and third plates, respectively.

13. The expandable intervertebral implant as recited in claim 1, wherein the inferior component further comprises one or more first openings and the superior component further comprises one or more second openings.

14. The expandable intervertebral implant as recited in claim 1, wherein the second, third, fifth, and sixth plates are curvilinear such that the superior component can expand from the inferior component in a curvilinear direction.

15. An expandable intervertebral implant, comprising:
an inferior component, including:
 a first plate;
 a second plate connected to the first plate and comprising a first plurality of locking apertures; and,
 a third plate connected to the first plate and comprising a second plurality of locking apertures;

a superior component slidingly engaged with the inferior component, including;
  a fourth plate;
  a fifth plate connected to the fourth plate and comprising a third locking aperture, the fourth plate arranged adjacent the second plate; and,
  a sixth plate connected to the fourth plate and comprising a fourth locking aperture, the sixth plate arranged adjacent the third plate; and,
a locking pin assembly, including:
  a shaft having a first end and a second end;
  a first engaging member sliding engaged with the first end and arranged at least partially in the third locking aperture;
  a second engaging member sliding engaged with the second end and arranged at least partially in the fourth locking aperture; and,
  at least one spring arranged axially between the first and second engaging members;
  wherein the first and second engaging members are operatively arranged to engage the first and second pluralities of locking apertures to lock the expandable intervertebral implant.

16. The expandable intervertebral implant as recited in claim 15, wherein:
the second and third plates are arranged substantially perpendicular to the first plate; and,
the fifth and sixth plates are arranged substantially perpendicular to the third plate.

17. The expandable intervertebral implant as recited in claim 15, wherein:
the first engaging member is biased toward the first plurality of locking apertures by a first spring; and,
the second engaging member is biased toward the second plurality of locking apertures by a second spring.

18. The expandable intervertebral implant as recited in claim 17, wherein:
the first engaging member comprises a first flange engaged with the first spring and a first pin extending from the first flange; and,
the second engaging member comprises a second flange engaged with the second spring and a second pin extending from the second flange.

19. The expandable intervertebral implant as recited in claim 18, wherein:
the first pin includes a first beveled surface; and,
the second pin includes a second beveled surface.

20. The expandable intervertebral implant as recited in claim 15, wherein:
the second plate includes at least one first vertical flange; and,
the third plate includes at least one second vertical flange.

21. The expandable intervertebral implant as recited in claim 20, wherein:
the fifth and sixth plates are arranged axially between the second and third plates;
the at least one first vertical flange forms a guide for the fifth plate; and,
the at least one second vertical flange forms a guide for the sixth plate.

22. An expandable intervertebral implant, comprising:
an inferior component, including:
  a first plate;
  a second plate connected to the first plate and comprising a first plurality of locking apertures; and,
  a third plate connected to the first plate and comprising a second plurality of locking apertures;
a superior component slidingly engaged with the inferior component, including;
  a fourth plate;
  a fifth plate connected to the fourth plate and comprising a third locking aperture; and,
  a sixth plate connected to the fourth plate and comprising a fourth locking aperture; and,
a locking pin assembly:
comprising:
  a shaft including a first end and a second end;
  a first spring arranged on the first end;
  a second spring arranged on the second end;
  a first engaging member slidingly engaged with the first end; and,
  a second engaging member slidingly engaged with the second end;
arranged at least partially in the third and fourth locking apertures; and,
operatively arranged to engage the first and second pluralities of locking apertures to lock the expandable intervertebral implant.

* * * * *